United States Patent
Strömbom et al.

(10) Patent No.: US 6,673,981 B1
(45) Date of Patent: Jan. 6, 2004

(54) ABSORBENT STRUCTURE IN AN ABSORBENT ARTICLE

(75) Inventors: Eva Strömbom, Mölndal (SE); Shabira Abbas, Göteborg (SE); Camilla Bemm, Göteborg (SE); Åsa Östman, Göteborg (SE); Jeanette Annergren, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/651,128

(22) Filed: Aug. 30, 2000

Related U.S. Application Data

(60) Provisional application No. 60/198,454, filed on Apr. 19, 2000.

(30) Foreign Application Priority Data

Aug. 30, 1999 (SE) .................................................. 9903072

(51) Int. Cl.[7] .................................................. A61F 13/15
(52) U.S. Cl. ........................ 604/368; 604/378; 604/369
(58) Field of Search .................................. 604/364, 367, 604/368, 378, 379, 380, 369

(56) References Cited

U.S. PATENT DOCUMENTS

| | | |
|---|---|---|
| 3,512,450 A | 5/1970 | Portal |
| 4,957,810 A | 9/1990 | Eleouet et al. |
| 5,338,766 A | 8/1994 | Phan et al. |
| 5,506,035 A * | 4/1996 | Van Phan et al. ............ 428/196 |
| 5,817,081 A * | 10/1998 | LaVon et al. ................ 604/378 |
| 6,033,769 A * | 3/2000 | Brueggemann et al. .. 428/305.5 |
| 6,093,870 A * | 7/2000 | Carlsson ..................... 604/368 |

FOREIGN PATENT DOCUMENTS

| | | |
|---|---|---|
| EP | 0 212 618 | 3/1987 |
| EP | 0 293 208 | 11/1988 |
| EP | 0 478 011 | 4/1992 |
| EP | 0 532 002 | 3/1993 |
| EP | 0 804 913 | 11/1997 |
| WO | 97/32612 | 9/1997 |

* cited by examiner

*Primary Examiner*—Weilun Lo
*Assistant Examiner*—Michael G. Bogart
(74) *Attorney, Agent, or Firm*—Burns Doane Swecker & Mathis LLP

(57) ABSTRACT

An absorbent porous structure for use in a diaper, a pant diaper, an incontinence guard, a sanitary napkin or the like, with a liquid acquisition portion and a liquid storage portion which are an integrated unit. The liquid acquisition portion comprises a compressed polymeric open-cell foam which expands upon wetting, and the liquid storage portion comprises a polymeric open-cell foam which may be the same or different from the foam in the liquid acquisition portion. The liquid storage portion also contains a superabsorbent material, with the amount of superabsorbent material being lower in the part of the liquid storage portion that is located closest to the liquid acquisition portion than in the part of the liquid storage portion that is located furthest from the liquid acquisition portion. Other embodiments include a method for producing the absorbent structure and an absorbent article containing such an absorbent structure.

16 Claims, 4 Drawing Sheets

ABSORBENT STRUCTURE IN AN ABSORBENT ARTICLE

This application claims the benefit of U.S. Provisional Application No. 60/198,454, filed on Apr. 19, 2000, the entire content of which is hereby incorporated by reference.

TECHNICAL FIELD

The present invention refers to an absorbent structure in an absorbent article such as a diaper, a pant diaper, an incontinence guard, a sanitary napkin etc. said absorbent structure comprises a compressed foam, which expands upon wetting. The invention further refers to a method of producing an absorbent article containing an absorbent structure according to the invention.

BACKGROUND

Absorbent articles of the above mentioned kind are intended to absorb body liquids such as urine and blood. Such absorbent articles usually have a liquid pervious topsheet, which during use is facing the wearer's body. They further have a liquid impervious backsheet, e g a plastic film, a plastic coated nonwoven or a hydrophobic nonwoven, and an absorbent structure enclosed between the liquid pervious topsheet and the liquid impervious backsheet. The absorbent structure may comprise two or more layers such as liquid acquisition layer, storage layer and distribution layer.

It is desired that absorbent articles of the above mentioned kind are thin and discrete to use. It is further important that absorbent articles of the above mentioned kind have a high liquid acquisition capacity as well as liquid distributing and liquid storing capacity.

In order to obtain a good liquid acquisition capacity it is important that the liquid acquisition layer has a high momentaneous liquid acquisition capacity. Open, bulky structures with large capillaries have a high momentaneous liquid acquisition capacity and examples of such material are cellulosic fluff pulp of thermomechanic or chenithermomechanic (CTMP) type, chemically stiffened cellulosic fibers, synthetic fiber structures of different kind and porous foam materials.

It is previously known through U.S. Pat. No. 3,512,450, EP-A-0 293 208 and EP-A-0 804 913 to use a compressed foam material of regenerated cellulose, e g viscose, as an absorbent structure in an absorbent article of the above mentioned kind, e g a sanitary napkin. The article may then be made very thin and still have a high absorption capacity. The compressed viscose foam expands quickly i the z-direction when liquid is absorbed by the material when wetted. From EP-A-0 293 208 it is further known that such an absorbent structure can contain superabsorbent material.

As storage layer it is commonly used cellulosic fluff pulp with admixture of super-absorbents, i e crosslinked polymers with the ability to absorb liquid several times their own weight. In order to obtain a thin diaper with a maintained total absorption capacity, it is desired to increase the amount of superabsorbent material in the fluff pulp network. In order to make it possible to increase the amount of superabsorbent material it is for example through EP 0 532 002 in absorbent structures known to use superabsorbent material having a good liquid distributing capacity.

Through EP 0 212 618 and EP 0 478 011 it is known to use an absorbent structure that seen in its thickness direction has a gradually increasing concentration of super-absorbent particles, at which a higher concentration of superabsorbent material is localized to the portion of the absorbent structure that during use is placed closest to the liquid impervious backsheet. The use of such a structure attempts to reduce the risk for gelblocking and to improve liquid distribution. One problem with such a structure is that from a processability point of view it is difficult to apply the superabsorbent particles so that a gradually increasing particle concentration is achieved in the thickness direction.

DESCRIPTION OF THE INVENTION

The problem of providing an absorbent article which is comfortable and discrete to wear, at the same time as it has both a high liquid acquisition capacity and a high liquid distribution capacity, has been substantially eliminated by the present invention.

According to the invention there is provided an absorbent porous structure for use in a diaper, a pant diaper, an incontinence guard, a sanitary napkin etc. and which is provided with a liquid acquisition portion and a liquid storage portion, at which the liquid acquisition portion comprises a compressed polymeric open-cell foam which expands upon wetting, and which is characterized by the liquid acquisition portion and the liquid storage portion being an integrated unit, at which the liquid storage portion comprises a polymeric open-cell foam which may be the same or different from the foam in the liquid acquisition portion, and that the liquid storage portion also contains a superabsorbent material. In the portion of the liquid storage portion that is located closest to the liquid acquisition portion the amount of superabsorbent material is lower than in the portion of the liquid storage portion that is located furthest away from the liquid acquisition portion. One advantage of the invention is that the total absorption capacity of the absorbent structure is utilized to a higher degree than if the amount of superabsorbent material is the same in the entire liquid storage layer. In the upper part of the liquid storage layer it is important that the liquid has the ability to be distributed in the longitudinal direction of the structure from the longitudinal mid portion of the structure which coincides with the wetting area, out towards the longitudinal end portions of the absorbent structure. In the lower part of the liquid storage portion it is however mainly important that the absorption capacity is so high that the article has the ability to store so much liquid as possible without leaking.

Thus with the present invention there is obtained an integrated absorbent structure which has a high liquid acquisition capacity as well as a high liquid distribution and liquid storage capacity. An integrated absorbent structure is more advantageous than an absorbent structure comprising different layers since the joining step is eliminated, making the structure cheaper to manufacture. The problem of having a bad liquid transfer layer between different layers is further eliminated in an integrated structure. The reason for usually having a worse liquid transfer between different layers than in an integrated structure is that it is difficult to achieve a sufficiently good contact between different layers. Another advantage relating to a foam absorbent structure is that it is more flexible and pliable than a fibrous structure. Another advantage with a foam-formed structure is that it is easier to provide a uniform basis weight in the longitudinal and transverse direction of the structure. It has however proved to be difficult to provide a matformed fiber structure having a sufficiently uniform basis weight.

According to a preferred embodiment the amount of superabsorbent material increases gradually in the z-direction of the of the liquid storage portion from the part of the liquid storage portion that is located closest to the liquid acquisition portion to the part of the liquid storage portion that is located furthest away from the liquid acquisition portion. Such an embodiment is advantageous since it reduces the risk for gelblocking farther.

According to one embodiment the portion of the liquid storage portion that as seen in the z-direction is located remote from the liquid acquisition portion only comprises superabsorbent material.

According to an embodiment the superabsorbent material is a porous open-cell foam structure. The advantage of having the superabsorbent material in the form of a foam, is that it is possible to obtain liquid transport between the pores in the superabsorbent material. It is especially important that the superabsorbent material per se has the ability to transport liquid when the amount of superabsorbent is high, i e in the lower part of the liquid storage portion. When the superabsorbent material is in the form of an open-cell foam structure it is also possible that the absorbent material according to the invention only consists of the superabsorbent material. It is also possible that the superabsorbent material comprises a film-forming polymer, which forms a film coating on the pore walls of the foam. Another advantage of having the superabsorbent material in the form of a foam or a film-forming coating, is that such a Structure is easy to produce since the difficulties of applying superabsorbent particles in a thickness gradient are eliminated. In such a structure the problem of dusting caused by the smallest superabsorbent particles in the manufacture is eliminated.

The superabsorbent material can for example be based on polyacrylate. It is also possible that the superabsorbent material is based on cellulose or starch.

According to a preferred embodiment the compressed foam structure comprises a regenerated cellulose structure, so called viscose foam. An advantage with a foam of regenerated cellulose is that such a foam when wetted has a very high swelling ability in the z-direction of the structure. This involves that such an article can be very thin before wetting. It is also an advantageous material for articles that are to be shaped into a three-dimensional shape upon wetting, such as for example hump-shaped sanitary napkins. By the fact that the three-dimensional shape appears upon wetting it is possible to produce articles that still are thin and discrete before use.

According to an embodiment the regenerated cellulose foam structure also includes fibers. By incorporating fibrous elements in the regenerated foam structure an improved liquid distributing capacity is achieved.

According to one embodiment the foam structure in the liquid acquisition portion is in dry condition more compressed than the foam structure in the liquid storage portion.

The invention also refers to a method for producing an absorbent structure according to the invention. Such a structure is obtained by shaping a foam material, which is compressed and then dried. After drying the structure a monomer solution of superabsorbent material is added to one of the opposite sides of the foam material, as seen in the z-direction, at which the part of the compressed foam that is wetted by the monomer solution expands. The polymer solution is then polymerized and crosslinked. The structure may optionally be compressed further, after which it is finally dried.

The invention also refers to an absorbent article such as incontinence guard, diaper, pant diaper, sanitary napkin and the like and of the kind comprising a liquid pervious topsheet, a liquid Impervious backsheet and an absorbent structure applied there-between, said absorbent structure containing a structure as disclosed above.

DESCRIPTION OF EMBODIMENTS

Figure 1:
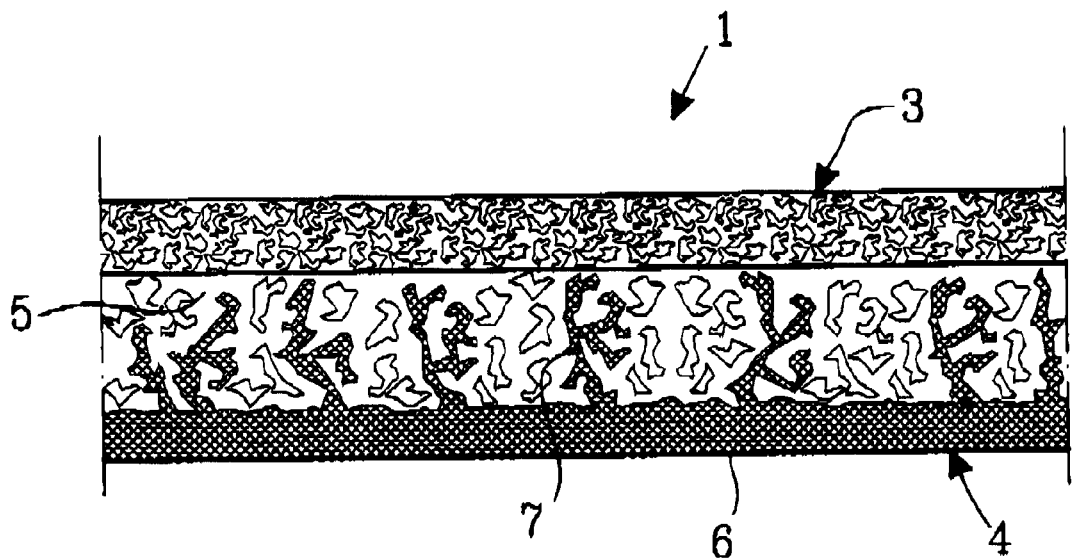
FIG. 1 shows a schematic cross-section through an absorbent structure according to the invention in compressed form, in which the structure in z-direction comprises a liquid acquisition portion and a liquid storage portion.

The integrated absorbent structure 1 comprises (seen in the in z-direction) a liquid acquisition portion 3 and a liquid storage portion 4. The liquid acquisition portion 3 and the liquid storage portion 4 comprise a compressed foam material, which upon liquid contact expands strongly under simultaneous absorption of liquid. An example of such a foam material is regenerated cellulose. The foam material in the liquid storage portion 4 also comprises a superabsorbent material. When manufacturing the absorbent structure a monomer solution of the superabsorbent is added to one side of the compressed foam. Upon application of the monomer solution to the compressed foam this will expand in the area which is wetted by the monomer solution. This involves that the foam material in the liquid storage portion in dry condition is not so strongly compressed as the foam material in the liquid acquisition portion. The amount of superabsorbent material in the liquid storage portion 4 is lowest closest to the liquid acquisition portion and highest furthest away from the liquid acquisition portion. The liquid storage portion 4 in the absorbent structure in FIG. 1 comprises, as seen in the z-direction, two different portions 5,6. The first portion 5 is located adjacent the liquid acquisition portion 3 and the other portion is located remote from the liquid acquisition portion 3. The first portion 5 comprises the compressed foam, at which the superabsorbent material is placed in the open cells 7 of one part of the porous compressed foam. The other portion 6 consists of only the superabsorbent material. The superabsorbent material is preferably in the form of a foam, but it is also possible that it is in the form of a film-forming gel. The liquid storage portion can of course also consist of only the first portion 5, at which the amount of superabsorbent material decreases towards the liquid acquisition portion.

Figure 2:
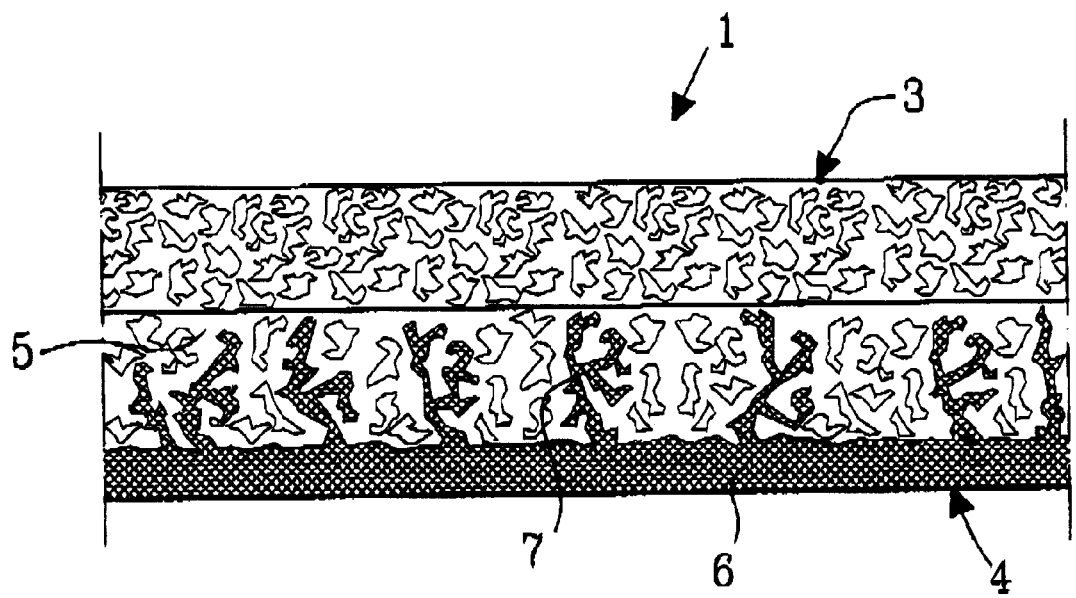
FIG. 2 shows the absorbent structure according to FIG. 1 in expanded form.

FIG. 2 shows the absorbent structure according to FIG. 1 in expanded form, i.e. when the absorbent structure has been wetted during use of the absorbent structure in an absorbent article. The liquid acquisition portion 3 and the liquid storage portion 4 have expanded in the z-direction. The liquid acquisition portion 3 which in dry condition is more compressed than the liquid storage portion 4 has thus expanded more than the liquid storage portion 4.

The amount of superabsorbent material in the liquid storage portion is over 20 weight percent, based on the total weight of the liquid storage portion in dry condition. Preferably the amount of superabsorbent material is over 50 weight percent in the liquid storage portion.

When manufacturing the absorbent porous structure a foam material is formed, which is compressed and then dried. After that a monomer solution of the superabsorbent material is applied to one of the opposite sides of the foam material, as seen in the z-direction. Then the monomer solution is polymerized and crosslinked. The part of the compressed foam which is wetted by the monomer solution is somewhat expanded, while the part of the compressed foam that, as seen in the z direction, is located furthest away from the side wetted by the monomer solution, is not wetted and therefore not expands. Since the liquid acquisition portion consists of the part of the compressed foam that, as seen in the z-direction, is located furthest away from the side wetted by the monomer solution, and thus is more compressed, a more rapid liquid acquisition is obtained In the liquid acquisition portion than in the liquid distribution portion. It is also possible to compress the structure further after application of the superabsorbent material.

The monomer solution can be in the form of a solution which upon application on the compressed foam trickles down into the open pores of the compressed foam and forms a filmlike coating. By the fact that a part of the monomer solution trickles into and penetrates part of the open pore system of the compressed foam, there will be obtained a gradually decreasing amount of superabsorbent material in the liquid storage portion of the foam material in the direction away from the side on which the monomer solution has been applied, i e there will be a gradually increasing amount of superabsorbent in the liquid storage portion 4 in the direction away from the liquid acquisition portion 3. The monomer solution can also be in the form of a foamed dispersion solution which after application against one side of the compressed foam is polymerized and crosslinked. The advantage of applying the superabsorbent material in the form of a foamed dispersion solution is that a porous structure is also formed of the superabsorbent material, which involves that the liquid transport in the liquid storage portion is improved. By applying the superabsorbent material in the form of a foamed dispersion solution it is also possible to provide a liquid storage portion which to 100% consists of the superabsorbent material.

It is further possible that the entire absorbent porous structure, i e both the liquid storage portion and the liquid acquisition portion, to 100% consists of a compressed superabsorbent foam. In order to obtain good liquid acquisition properties in the liquid acquisition layer the superabsorbent material in this layer is highly crosslinked. A very highly cross-linked superabsorbent material can not receive so much liquid as a super-absorbent having a lower degree of crosslinking, but on the other side a highly crosslinked superaborbent is better to maintain liquid under pressure. The liquid storage portion in such a structure is crosslinked to a lower degree.

According to a preferred embodiment the foam material is regenerated cellulose, such as viscose, which is a foam comprising a skeleton of cellulose, An advantage of having a foam material of regenerated cellulose is that such a structure has a higher stiffness than foam structures of superabsorbent material based on polyacrylate. Foam materials of regenerated cellulose herewith create firmness to the liquid storage portion.

The principle of making a porous viscose foam is known since long ago and shortly takes place in the following way. Cellulose, usually sulphite pulp, is allowed to swell in sodium hydroxide. Carbon disulphide is added at which the cellulose is successively dissolved. In order to improve the mechanical strength in the material for example cotton fibers may be added. To this cellulose solution there is added and dispersed a salt in the form of sodium sulphate. When then the solution is heated the cellulosed is regenerated (the carbon disulphide is evaporated) and the salt (sodium sulphate ) is dissolved by washing the material with water at which a porous spongelike structure is obtained. The material is dried and compressed if desired It is also possible to provide an absorbent structure which in its thickness direction has a pore size gradient. In order to provide such a pore size gradient different viscose solutions are used, which are applied on top of each other and then regenerated. Sodium sulphate with different particle sizes is used in the different layers, at which a different pore size of the foam is obtained. By the fact that the different layers are placed on top of each other before they are dry there is achieved an integrated structure, in which the layers partly penetrate into each other.

After regeneration of the cellulose and washing for removing the salt particles the material is dried and compressed to the desired density, which should be in the interval 0.1 to 2.0 g/cm$^3$. The material will upon liquid absorption expand quickly in volume from 2 to 20 times, preferably from 2 to 15 times its volume in compressed condition. The increase of volume at the absorption mainly occurs in the compression direction, i e in the z-direction of the material.

In order to provide a viscose foam containing a certain amount of fibers that are anchored to the pore walls of the foam, fibers can be added to the viscose solution before the foam is shaped. It is also possible to interrupt the dissolving of the cellulose fibers at the addition of the carbon disulphide, so that all fibers are not dissolved. The dissolving can for example be interrupted when 50 weight percent of the cellulose fibers have been dissolved, based on the total dry weight of the cellulose fibers.

The foam may of course be of an optional polymeric material and it is possible to create different mean pore sizes of the respective foam layers by other methods than described above by means of salt crystals of different particle sizes. One such alternative way is to use different types of foaming agents when producing the different foam layers, and which provide different mean pore sizes. Another way is to influence the foaming process in such a way, c g by heating the different layers to different degrees during foaming. In this case it would be possible to use the same foaming agent in the different layers.

The foam materials in the liquid acquisition layer 3 and the liquid storage layer 4 respectively can be the same. It is however also possible to use different foam materials in the different layers, at which for example a hydrophilicity gradient would be created in the z-direction by having foams of different hydrophilicity/hydrophobicty in the different layers 3 and 4 respectively.

Figure 3:
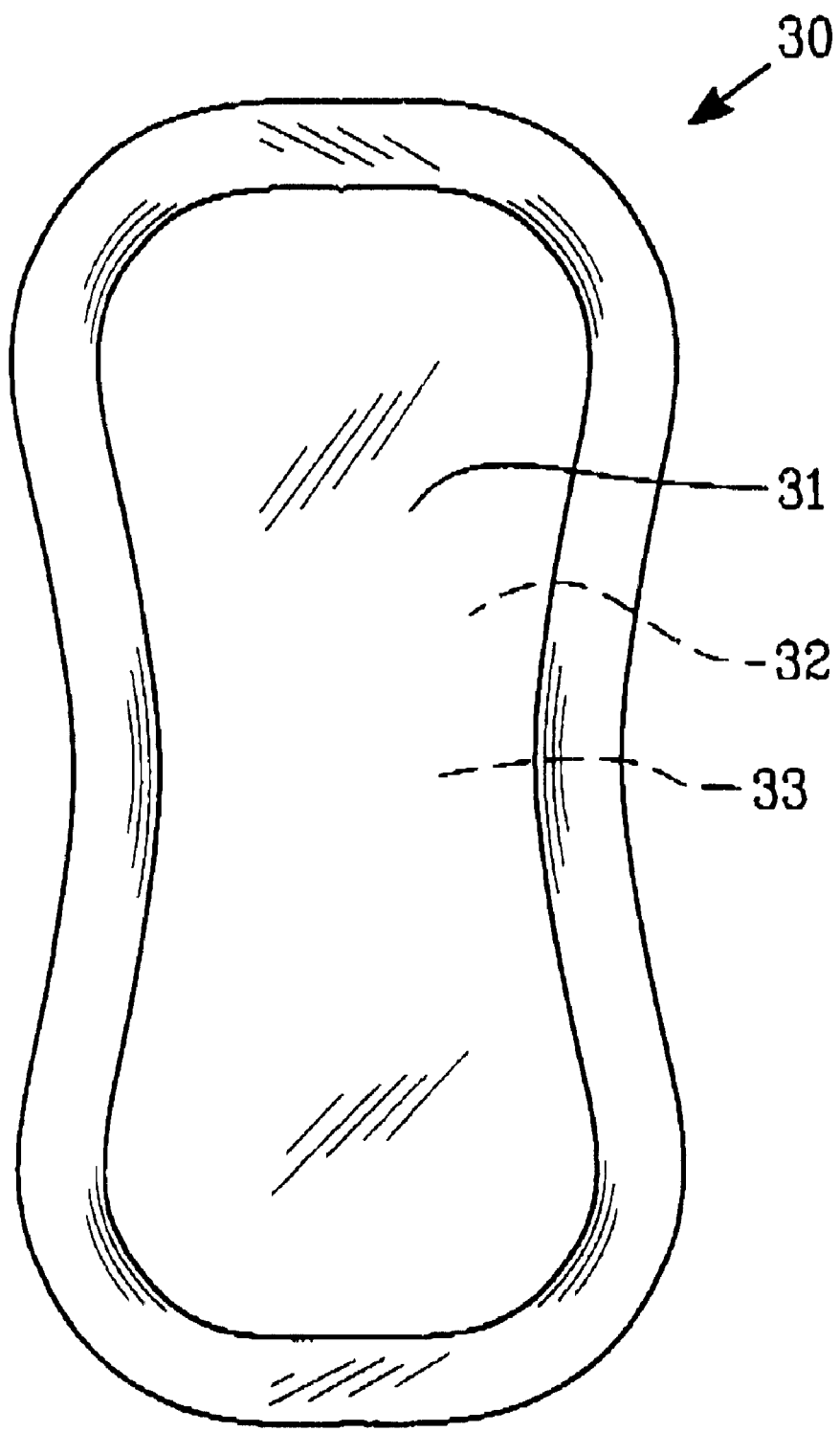
FIG. 3 shows in a view from above an absorbent article in the form of an incontinence guard.
Figure 4:
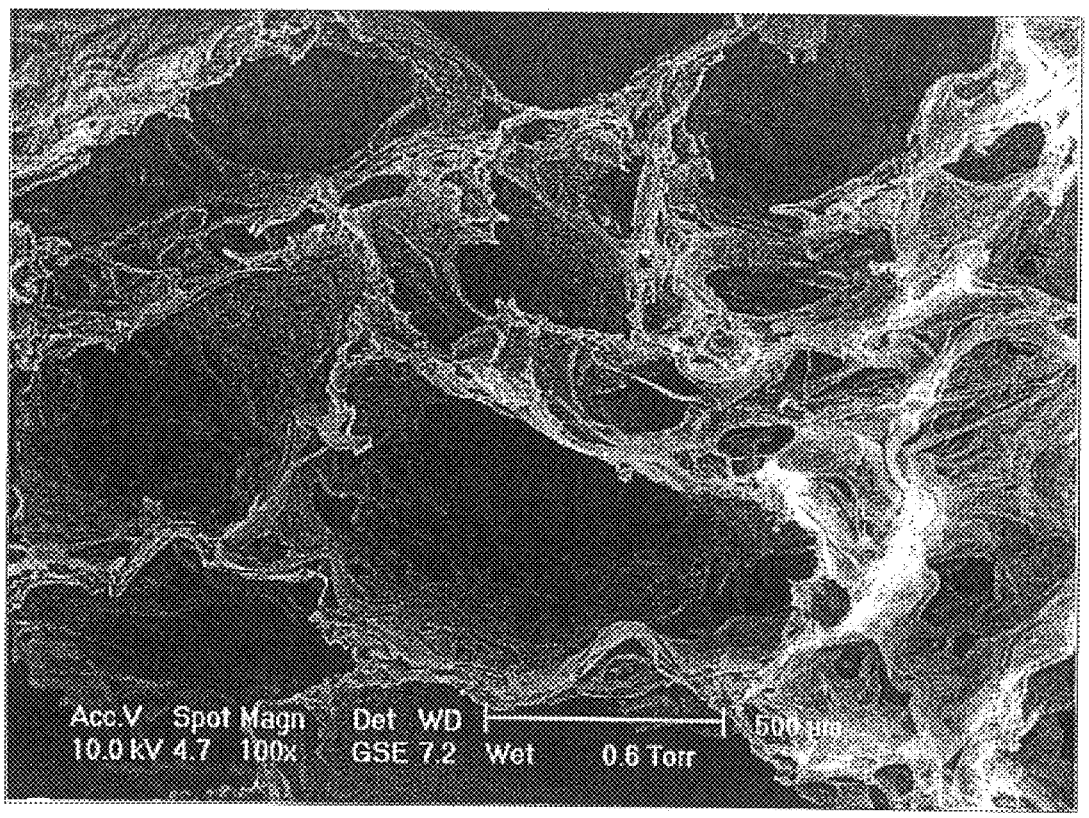
FIG. 4 shows an electron microscope picture (ESEM) of a viscose foam without a superabsorbent film forming coating.
Figure 5:
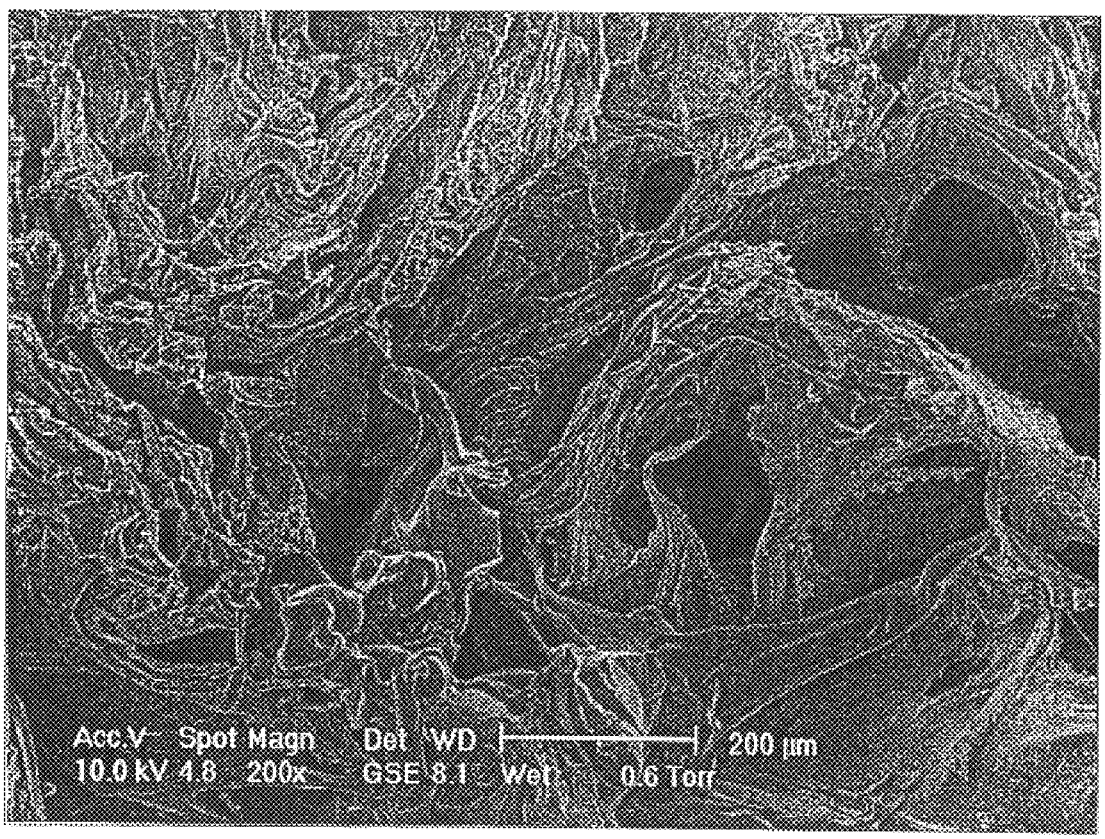
FIG. 5 shows an electron microscope picture (ESEM) of a viscose foam according to the invention with a superabsorbent film forming coating.

In FIG. 3 there is shown an absorbent article 30 in the form of an incontinence guard comprising a liquid pervious topsheet 31, a liquid impervious backsheet 32 and absorbent structure 33 according to the invention applied therebetween. The liquid pervious topsheet 31 may be a nonwoven material, e g a spunbond material of synthetic filaments, a thermobonded material, e g a bonded carded fibrous material or a perforated plastic film. The liquid impervious backsheet 32 usually consists of a plastic film, a nonwoven material coated with a liquid impervious material or a hydrophobic nonwoven which resists liquid penetration. The topsheet 31 and the backsheet 32 has a somewhat larger extension in the plane than the absorbent structure 33 and extends outside the edges thereof. The layers 31 and 32 are interconnected within the projecting portions, for example by gluing or welding with heat or ultrasonic.

It is noted that an incontinence guard according to the invention is not limited to embodiment show in the drawing, but the shape of the article as well as its overall design can be varied. The absorbent article can also comprise a diaper, a pant diaper, a sanitary napkin, a bed protection or the like.

The absorbent structure according to the invention may also be arranged over only a part of the total surface of the absorbent body of the absorbent article, e g at the intended wetting area where the discharged body fluid will be deposited and which usually is located towards the front part of the article. The portions of the absorbent body located outside the intended wetting area may then be of another optional absorbent material. It is also possible that the liquid acquisition portion is only located over the area which is intended to be the wetting area, while the liquid storage portion is arranged over the entire surface of the absorbent structure. Such an embodiment is especially preferred when using the absorbent structure in a sanitary napkin. The liquid acquisition portion swells upon discharge of liquid in the z-direction and forms a hump.

The invention is of course not limited to the above mentioned embodiments, but may of course be applied in other embodiments within the scope of the following claims.

What is claimed is:

1. An absorbent porous structure in an absorbent article, said absorbent porous structure comprising a liquid acquisition portion and a liquid storage portion, the liquid acquisition portion comprising a compressed polymeric open-cell foam which expands upon wetting, wherein the liquid acquisition portion and the liquid storage portion are an integrated unit, the liquid storage portion comprising a polymeric open-cell foam which may be the same or different from the foam in the liquid acquisition portion and a superabsorbent material, wherein an amount of superabsorbent material is lower in a part of the liquid storage portion that is located closest to the liquid acquisition portion than in a part of the liquid storage portion that is remote from the liquid acquisition portion.

2. An absorbent structure as claimed in claim 1, wherein an amount of superabsorbent material in a z-direction of the liquid storage portion gradually increases from the part of the liquid storage portion that is located closest to the liquid acquisition portion to a part of the liquid storage portion that is located furthest away from the liquid acquisition portion.

3. An absorbent structure as claimed in claim 1, wherein a part of the liquid storage portion in a z-direction of the absorbent article that is located furthest away from the liquid acquisition portion only consists of the superabsorbent material.

4. An absorbent structure as claimed in claim 1, wherein the superabsorbent material is a foam.

5. An absorbent structure as claimed in claim 1, wherein the superabsorbent material is a film-forming polymer forming a film coating on pore walls of the foam.

6. An absorbent structure as claimed claim 1, wherein the superabsorbent material is based on polyacrylate.

7. An absorbent structure as claimed in claim 1, wherein the superabsorbent material is based on cellulose or starch.

8. An absorbent structure as claimed in claim 1, wherein the compressed foam is a regenerated cellulose structure.

9. An absorbent structure as claimed in claim 8, wherein the regenerated cellulose structure also comprises fibers.

10. An absorbent structure as claimed in claim 1, wherein a foam structure in the liquid acquisition portion in a dry condition is more compressed than a foam structure in the liquid storage portion in a dry condition.

11. An absorbent article comprising a liquid pervious topsheet, a liquid impervious backsheet and an absorbent structure as claimed in claim 1 arranged therebetween.

12. An absorbent structure in an absorbent article as in claim 1, wherein the absorbent article is a diaper, a pant diaper, an incontinence guard, or a sanitary napkin.

13. An absorbent article as in claim 11, wherein the absorbent article is a diaper, a pant diaper, an incontinence guard, or a sanitary napkin.

14. An absorbent structure as claimed in claim 1, wherein the liquid acquisition portion and the liquid storage portion partly penetrate into each other.

15. An absorbent porous structure in an absorbent article, said absorbent porous structure comprising a liquid acquisition portion and a liquid storage portion, the liquid acquisition portion comprising a compressed polymeric open-cell foam which expands upon wetting, the liquid acquisition portion and the liquid storage portion are an integrated unit, the liquid storage portion comprising a polymeric open-cell foam which may be the same or different from the foam in the liquid acquisition portion and a superabsorbent material, wherein an amount of superabsorbent material is lower in a part of the liquid storage portion that is located closest to the liquid acquisition portion than in a part of the liquid storage portion that is furthest away from the liquid acquisition portion, the amount of superabsorbent material in a z-direction of the liquid storage portion gradually increases from the part of the liquid storage portion that is located closest to the liquid acquisition portion to the part of the liquid storage portion that is located furthest away from the liquid acquisition portion, and the superabsorbent material is a foam or a film-forming polymer forming a film coating on pore walls of the polymeric open-cell foam of the liquid acquisition portion and the liquid storage portion.

16. An absorbent structure as claimed in claim 15, wherein the liquid acquisition portion and the liquid storage portion partly penetrate into each other.

* * * * *